(12) United States Patent
Sakikawa

(10) Patent No.: US 11,833,321 B2
(45) Date of Patent: Dec. 5, 2023

(54) APPLICATION MEMBER AND IMPREGNATION MATERIAL

(71) Applicant: SHARP KABUSHIKI KAISHA, Sakai (JP)

(72) Inventor: Nobuki Sakikawa, Osaka (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 54 days.

(21) Appl. No.: 17/635,833

(22) PCT Filed: Sep. 23, 2020

(86) PCT No.: PCT/JP2020/035657
§ 371 (c)(1),
(2) Date: Feb. 16, 2022

(87) PCT Pub. No.: WO2021/060224
PCT Pub. Date: Apr. 1, 2021

(65) Prior Publication Data
US 2022/0288368 A1    Sep. 15, 2022

(30) Foreign Application Priority Data
Sep. 27, 2019  (JP) ................. 2019-177956

(51) Int. Cl.
| | | |
|---|---|---|
| A61M 35/00 | (2006.01) | |
| A45D 34/04 | (2006.01) | |
| B01J 20/26 | (2006.01) | |
| B01J 20/32 | (2006.01) | |
| A61K 8/02 | (2006.01) | |
| A61Q 19/00 | (2006.01) | |

(52) U.S. Cl.
CPC .......... *A61M 35/006* (2013.01); *A45D 34/04* (2013.01); *B01J 20/26* (2013.01); *B01J 20/3285* (2013.01); *A61K 8/0208* (2013.01); *A61Q 19/00* (2013.01)

(58) Field of Classification Search
CPC ....... A61M 35/006; A45D 34/04; B01J 20/26; B01J 20/3285; A61K 8/0208; A61K 8/731; A61K 8/8129; A61Q 19/00
USPC .................... 541/63, 847, 781, 786
See application file for complete search history.

(56) References Cited

U.S. PATENT DOCUMENTS 5,420,118 A * 5/1995 Alban ............... A61K 8/8152
                                                    514/738
10,406,079 B2 * 9/2019 Song ..................... A61Q 19/00
2006/0286152 A1 12/2006 Hu et al.

FOREIGN PATENT DOCUMENTS

| JP | 2008-546723 A | 12/2008 |
| JP | 2009-292786 A | 12/2009 |

* cited by examiner

*Primary Examiner* — David J Walczak
(74) *Attorney, Agent, or Firm* — ScienBiziP, P.C.

(57) ABSTRACT

An application member includes a stimuli-responsive polymer that reversibly changes to being hydrophilic and to being hydrophobic in response to an external stimulus to allow impregnation and release of an active ingredient to be applied to the skin.

6 Claims, 10 Drawing Sheets

APPLICATION MEMBER AND IMPREGNATION MATERIAL

TECHNICAL FIELD

One aspect of the present invention relates to an application member that can perform impregnation of an active ingredient and an impregnation material that is impregnated with the active ingredient. The present application claims priority from JP 2019-177956 filed in Japan on Sep. 27, 2019, the content of which is hereby incorporated by reference into this application.

BACKGROUND ART

As described in JP 2009-292786 A, in order to apply a liquid component such as toner to the skin, a conventionally known product is obtained by impregnating an impregnation material such as a sponge with the liquid component.

SUMMARY OF INVENTION

However, in such a product, the impregnation material has to be pressed or rubbed against the skin in order to exude the liquid component from the impregnation material. As a result, there is a problem in that a strain is put on a sensitive skin.

An aspect of the present invention is directed to releasing an active ingredient in response to a body site, body temperature, or a stimulus such as heat or light, without applying an external force or with only the aid of slight external force.

In order to solve the above problem, an application member according to one aspect of the present invention includes a stimuli-responsive polymer that reversibly changes to being hydrophilic and to being hydrophobic in response to an external stimulus, so as to allow impregnation and release of an active ingredient to be applied to the skin.

In order to solve the above problem, an impregnation material according to another aspect of the present invention is impregnated with an active ingredient and includes a stimuli-responsive polymer gel absorbing the active ingredient in a state where a degree of an external stimulus is less than a predetermined level, while releasing the active ingredient in a state where the degree of the external stimulus is the level or greater.

According to an aspect of the present invention, it is possible to release an active ingredient in response to a body site, body temperature, or a stimulus such as heat or light, without applying an external force or with only the aid of slight external force.

DESCRIPTION OF EMBODIMENTS

Stimuli-Responsive Polymer Gel

Figure 1:
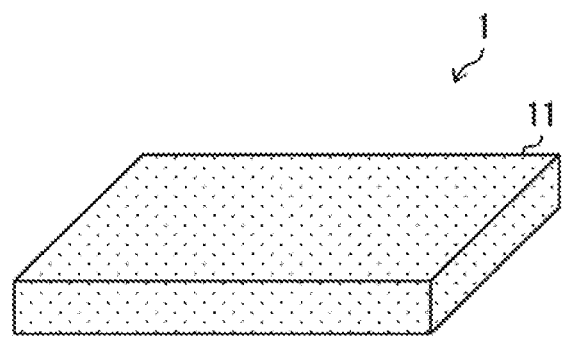
FIG. 1 is a perspective view illustrating a configuration of an impregnation material according to a first embodiment of the present invention.

A stimuli-responsive polymer gel includes a stimuli-responsive polymer whose affinity with water reversibly changes in response to an external stimulus, and a hydrophilic polymer. The stimuli-responsive polymer and the hydrophilic polymer form an interpenetrating polymer network (IPN) structure or semi-interpenetrating polymer network (semi-IPN) structure, or a random network structure or a block structure.

Here, the interpenetrating polymer network structure refers to a structure in which different types of polymers are cross-linked polymers and cross-linked networks of the respective polymers are mutually intertwined with each other in a state where the cross-linked networks are present independently without being chemically connected. The semi-interpenetrating polymer network structure refers to a structure in which one of the different types of polymers is a cross-linked polymer, the other is a linear polymer, and the polymers are mutually intertwined in a state where the polymers are present independently without being chemically connected.

In the former case, both the stimuli-responsive polymer and the hydrophilic polymer are cross-linked polymers each having a cross-linked network. In this case, the cross-linked network of the stimuli-responsive polymer and the cross-linked network of the hydrophilic polymer form a structure in which the cross-linked networks are mutually intertwined without being chemically connected, that is, the interpenetrating polymer network structure.

In the latter case, either the stimuli-responsive polymer or the hydrophilic polymer is a cross-linked polymer having a cross-linked network. In this case, the other is a linear polymer, and the stimuli-responsive polymer and the hydrophilic polymer form a structure in which the polymers are mutually intertwined without being chemically connected, that is, the semi-interpenetrating polymer network structure.

Alternatively, the stimuli-responsive polymer gel may be a copolymer having a random network structure or a block network structure including the stimuli-responsive polymer and the hydrophilic polymer. Furthermore, the stimuli-responsive polymer gel may be a copolymer of a single stimuli-responsive polymer or a plurality of stimuli-responsive polymers.

Stimuli-Responsive Polymer

A stimuli-responsive polymer refers to a polymer that reversibly changes its nature in response to an external stimulus. In the present embodiment, a stimuli-responsive polymer whose affinity with water reversibly changes in response to an external stimulus is used.

The external stimulus is not particularly limited, and examples thereof include heat, light, an electric field, and "Affinity with water reversibly changing in response to an external stimulus" means that a polymer that is exposed to an external stimulus reversibly changes between being hydrophilic and being hydrophobic in response to that external stimulus.

Among stimuli-responsive polymers, a stimuli-responsive polymer whose affinity with water reversibly changes in response to heat, that is, a temperature-responsive polymer, absorbs moisture and releases the absorbed moisture in a reversible manner due to a change in temperature. Such a temperature-responsive polymer is not particularly limited provided that the polymer has a lower critical solution temperature (LCST, in the description below, sometimes referred to as "LCST").

Temperature-Responsive Polymer

The temperature-responsive polymer exhibits hydrophilicity at a low temperature that is lower than the temperature sensitive point at which the temperature is at a predetermined level, that is, the LCST, and exhibits hydrophobicity at the temperature of the LCST or higher. Here, in a case where, when dissolved in water, the polymer is hydrophilic and dissolves at a low temperature but the polymer is hydrophobic and does not dissolve at a certain temperature or higher, the "LCST" refers to a temperature that acts as the boundary between temperatures.

More specific examples of the temperature-responsive polymer include: poly(N-alkyl (meth)acrylamide) such as poly(N-isopropyl (meth)acrylamide), poly(N-normalpropyl (meth)acrylamide), poly(N-methyl (meth)acrylamide), poly(N-ethyl (meth)acrylamide), poly(N-normalbutyl (meth)acrylamide), poly(N-isobutyl (meth)acrylamide), or poly(N-t-butyl (meth)acrylamide); poly(N-vinyl alkylamide) such as poly(N-vinyl isopropylamide), poly(N-vinyl normalpropylamide), poly(N-vinyl normalbutylamide), poly(N-vinyl isobutylamide), or poly(N-vinyl-t-butylamide); poly(N-vinylpyrrolidone); poly(2-alkyl-2-oxazoline) such as poly(2-ethyl-2-oxazoline), poly(2-isopropyl-2-oxazoline), or poly(2-normalpropyl-2-oxazoline); polyvinyl alkyl ethers such as polyvinyl methyl ether or polyvinyl ethyl ether; copolymers of polyethylene oxide and polypropylene oxide; poly(oxyethylene vinyl ether); cellulose derivatives such as methyl cellulose, ethyl cellulose, hydroxypropyl cellulose, hydroxypropyl methylcellulose, or hydroxyethyl cellulose; and copolymers of the polymers described above. The temperature-responsive polymer is more preferably a cross-linked body of these polymers. In particular, polymers of polysaccharides such as the cellulose derivatives described above are less irritating and are thus preferred because the product is brought into contact with human skin, as described below.

Here, in the present embodiment, as described above, the stimuli-responsive polymer and the hydrophilic polymer form the interpenetrating polymer network structure or the semi-interpenetrating polymer network structure. An example in which the stimuli-responsive polymer is a cross-linked body will be described below.

Examples of the cross-linked body of the temperature-responsive polymer include a polymer obtained by polymerizing, in the presence of a cross-linking agent, a monomer of: N-alkyl (meth)acrylamide such as N-isopropyl (meth)acrylamide, N-normalpropyl (meth)acrylamide, N-methyl (meth)acrylamide, N-ethyl (meth)acrylamide, N-normalbutyl (meth)acrylamide, N-isobutyl (meth)acrylamide, or N-t-butyl (meth)acrylamide; N-vinyl alkylamide such as N-vinyl isopropylamide, N-vinyl normalpropylamide, N-vinyl normal butylamide, N-vinyl isobutylamide, or N-vinyl-t-butylamide; a vinyl alkyl ether such as vinyl methyl ether or vinyl ethyl ether; ethylene oxide and propylene oxide; or 2-alkyl-2-oxazoline such as 2-ethyl-2-oxazoline, 2-isopropyl-2-oxazoline, or 2-normalpropyl-2-oxazoline, or two or more types of these monomers.

As the cross-linking agent, a conventionally known cross-linking agent only need be appropriately selected and used. As the cross-linking agent, for example, a cross-linkable monomer having a polymerizable functional group such as ethylene glycol di(meth)acrylate, propylene glycol di(meth)acrylate, N,N'-methylene bis(meth)acrylamide, tolylene diisocyanate, divinylbenzene, polyethylene glycol di(meth)acrylate; glutar aldehyde; polyhydric alcohol; polyvalent amine; polyvalent carboxylic acid; metal ions such as a calcium ion or a zinc ion, calcium chloride; or the like can be suitably used. These cross-linking agents may be used alone, or two or more of them may be used in combination.

Furthermore, the cross-linked body of the temperature-responsive polymer may be a cross-linked body obtained by reacting an uncross-linked temperature-responsive polymer, for example, the aforementioned temperature-responsive polymer, with the cross-linking agent described above to form a network structure.

Examples of a stimuli-responsive polymer whose affinity with water reversibly changes in response to light include: light-responsive polymers whose hydrophilicity or polarity changes due to light, such as an azobenzene derivative or a spiropyran derivative; copolymers of these polymers and at least one of a temperature-responsive polymer and a pH-responsive polymer; cross-linked bodies of the light-responsive polymers; and cross-linked bodies of the copolymers.

Furthermore, examples of a stimuli-responsive polymer whose affinity with water reversibly changes in response to an electric field include: polymers each having a dissociable group such as a carboxyl group, a sulfonic acid group, a phosphoric acid group, or an amino group; a polymer that forms a composite by electrostatic interaction, hydrogen bonding, or the like, such as a composite of a carboxyl group-containing polymer and an amino group-containing polymer; or a cross-linked body thereof.

In addition, examples of a stimuli-responsive polymer whose affinity with water reversibly changes in response to pH include: polymers each having a dissociable group such as a carboxyl group, a sulfonic acid group, a phosphoric acid group, or an amino group; a polymer that forms a composite by electrostatic interaction, hydrogen bonding, or the like, such as a composite of a carboxyl group-containing polymer and an amino group-containing polymer; or a cross-linked body thereof.

The molecular weight of the stimuli-responsive polymer is not particularly limited, but a number average molecular weight determined by gel permeation chromatography (GPC) is preferably 3000 or greater.

Hydrophilic Polymer

In the present embodiment, the hydrophilic polymer is not particularly limited as long as it is a hydrophilic polymer other than the stimuli-responsive polymer that forms the interpenetrating polymer network structure or the semi-interpenetrating polymer network structure together with the hydrophilic polymer.

Examples of the hydrophilic polymer include polymers each having a hydrophilic group such as a hydroxyl group, a carboxyl group, a sulfonic acid group, a phosphoric acid group, or an amino group in a side chain or a main chain. More specific examples of the hydrophilic polymer include: polysaccharides such as alginic acid or hyaluronic acid; chitosan; cellulose derivatives such as carboxymethyl cellulose, methyl cellulose, ethyl cellulose, or hydroxyethyl cellulose; copolymers of poly(meth)acrylic acid, polymaleic acid, polyvinyl sulfonic acid, polyvinyl benzenesulfonic acid, polyacrylamide alkylsulfonic acid, or polydimethylaminopropyl (meth)acrylamide, and (meth)acrylamide, hydroxyethyl (meth)acrylate, (meth)acrylic acid alkyl ester, or the like; a composite of polydimethylaminopropyl (meth)acrylamide and polyvinyl alcohol; a composite of polyvinyl alcohol and poly(meth)acrylic acid; poly (meth)acrylonitrile, polyallylamine, polyvinyl alcohol, polyethylene glycol, polypropylene glycol, poly (meth)acrylamide, poly-N, N'-dimethyl (meth)acrylamide, poly-2-hydroxyethyl methacrylate, poly-alkyl(meth)acrylate, polydimethylaminopropyl (meth)acrylamide, and poly(meth)acrylonitrile; and copolymers of the above polymers. The hydrophilic polymer is more preferably a cross-linked body thereof.

Here, in the present embodiment, as described above, the stimuli-responsive polymer and the hydrophilic polymer form the interpenetrating polymer network structure or the semi-interpenetrating polymer network structure. An example in which the hydrophilic polymer is a cross-linked body will be described below.

Examples of the cross-linked body of the hydrophilic polymer include a polymer obtained by polymerizing, in the presence of a cross-linking agent, a monomer such as (meth)acrylic acid, allyl amine, vinyl acetate, (meth)acrylamide, N,N'-dimethyl (meth)acrylamide, 2-hydroxyethyl methacrylate, alkyl (meth)acrylate, maleic acid, vinylsulfonic acid, vinylbenzenesulfonic acid, acrylamide alkylsufonic acid, dimethylaminopropyl (meth)acrylamide, or (meth)acrylonitrile.

As the cross-linking agent, a conventionally known cross-linking agent may be appropriately selected and used, and for example, a cross-linkable monomer having a polymerizable functional group such as ethylene glycol di(meth)acrylate, propylene glycol di(meth)acrylate, N,N'-methylene bis(meth)acrylamide, tolylene diisocyanate, divinylbenzene, or polyethylene glycol di(meth)acrylate; glutar aldehyde; polyhydric alcohol; polyvalent amine; polyvalent carboxylic acid; metal ions such as calcium iona or zinc ions, calcium chloride; and the like can be suitably used. These cross-linking agents may be used alone, or two or more of them may be used in combination.

Furthermore, the cross-linked body of the hydrophilic polymer may be a cross-linked body obtained by reacting, with the above cross-linking agent, the hydrophilic polymer that is not cross-linked, for example, a polymer obtained by polymerizing the above monomer, or a polysaccharide such as alginic acid or hyaluronic acid; chitosan; or a cellulose derivative such as carboxymethyl cellulose, methyl cellulose, ethyl cellulose, or hydroxyethyl cellulose to form a network structure.

The molecular weight of the hydrophilic polymer is not particularly limited, but a number average molecular weight determined by GPC is preferably 3000 or greater.

Impregnation Material

An impregnation material is made of the temperature-responsive polymer gel formed of the temperature-responsive polymer and the hydrophilic polymer. The impregnation material is impregnated with a solution containing an active ingredient, such as a serum or a chemical solution. The temperature-responsive polymer gel absorbs the solution when the temperature is less than the LCST, and releases the solution when the temperature is the LCST or higher.

The active ingredient is a component such as a cosmetically effective cosmetic ingredient or a pharmaceutically effective medicinal ingredient. Examples of the cosmetic ingredient include a moisturizing ingredient, an ultraviolet ray protective ingredient, a whitening ingredient, an anti-oxidant ingredient, a sebum control ingredient, and a deodorizing ingredient. Examples of the medicinal ingredient include an anti-inflammatory ingredient, an analgesic ingredient, a blood circulation promoting ingredient, an antiseptic ingredient, a vitamin, a steroid, and an antibiotic.

To impregnate the impregnation material with the solution, the impregnation material is immersed in the solution. Alternatively, the present invention is not limited thereto, and the solution may be sprayed on the impregnation material in view of ease of adjusting the impregnated amount of the solution. Alternatively, the solution may be mixed when the impregnation material is prepared. In this case, the impregnation material is a dried body, but as described below, absorbs moisture in the air to be in a wet state, and exhibits a mode similar to that when the impregnation material is impregnated with the solution.

Alternatively, even when the impregnation material is not a dried body and is in the following first to third swollen gel states, the impregnation material exhibits a mode similar to that when the impregnation material is impregnated with the solution. The first gel state is obtained by drying a gel prepared from a mixed solution of a material of the impregnation material and the solution and allowing the prepared gel to absorb moisture. The second gel state is obtained by maintaining a wet gel state in which the prepared gel is not dried. The third gel state is a state in which the stimuli-responsive gel, i.e., the impregnation material that is prepared without mixing an active ingredient is made as a dried body and the dried body is impregnated with a cosmetic/medicinal active ingredient.

By simply applying heat to the impregnation material impregnated with the active ingredient as described above, the impregnation material having absorbed moisture becomes hydrophobic and releases the active ingredient applied before or after preparation of the gel. For example, as the stimuli-responsive polymer gel, a temperature-responsive polymer gel having an LCST slightly lower than 37° C., which is a human body temperature, is used as the impregnation material. This allows the impregnation material to release and apply the solution to human skin by touching the skin when the temperature becomes the LCST or higher. This eliminates the need to press or rub the impregnation material against the skin to apply the active ingredient to the skin.

Note that the stimuli-responsive polymer gel used as the impregnation material is not limited to the temperature-responsive polymer gel, and may be a stimuli-responsive polymer gel that responds to a stimulus such as light, an electric field, or pH. For example, when a light-responsive polymer gel is used as the impregnation material, the impregnation material is in a swollen state in which the impregnation material retains the active ingredient when irradiated with only light having an intensity less than a predetermined intensity (level) (about the intensity of normal indoor illumination), and releases the solution when irradiated with light having the predetermined intensity or greater. In addition, the light-responsive polymer gel may reversibly change between being hydrophilic and being hydrophobic depending on the wavelength of the light.

The light-responsive polymer gel responds to light by itself, but may include a photothermal conversion material (photothermal converter such as carbon black or a conductive polymer) therein. The conductive polymer generates heat upon being subject to light. Such a light-responsive polymer gel converts light into heat by the photothermal conversion material and then causes a thereto-sensitive polymer gel to respond to the heat.

An embodiment of the impregnation material according to the present invention will be described below with reference to the drawings.

Method for Producing Impregnation Material

The impregnation material described above is produced by the following first to fifth production methods, for example.

In the first production method, first, a polymer gel is prepared by the method described in any one of (1) to (4) below (preparation step). In the methods described in (1) to (4) below, the stimuli-responsive polymer gel is prepared by cross-linking at least one of the stimuli-responsive polymer and the hydrophilic polymer.

(1) Each of the polymer material having stimuli responsiveness as described above and the hydrophilic polymer having strong moisture absorption/water absorption properties is cross-linked to form the interpenetrating polymer network (IPN) structure.

In this method, the monomer constituting the stimuli-responsive polymer is polymerized and cross-linked to form a cross-linked network of the cross-linked body of the stimuli-responsive polymer (first step), and the monomer constituting the hydrophilic polymer is polymerized and cross-linked in the presence of the cross-linked network (second step).

(2) Only one of the stimuli-responsive polymer and the hydrophilic polymeris cross-linked to form the semi-IPN structure.

In this method, the monomer constituting the stimuli-responsive polymer is polymerized and cross-linked to form a cross-linked network of the cross-linked body of the stimuli-responsive polymer (first step), and the monomer constituting the hydrophilic polymer is polymerized in the presence of the cross-linked network to form the semi-interpenetrating polymer network structure constituted by the cross-linked network and the linear hydrophilic polymer (second step). Alternatively, in the method described above, the monomer constituting the stimuli-responsive polymer is polymerized to produce a linear stimuli-responsive polymer (first step), and the monomer constituting the hydrophilic polymer is polymerized and cross-linked in the presence of the linear stimuli-responsive polymer to form the semi-interpenetrating polymer network structure constituted by the linear stimuli-responsive polymer and the cross-linked network of the cross-linked body of the hydrophilic polymer (second step).

(3) Only the stimuli-responsive polymer is cross-linked.

(4) Both the stimuli-responsive polymer and the hydrophilic polymer are cross-linked together (copolymerization).

In the methods described in (1) to (4), the polymerization method for polymerizing the monomer is not particularly limited, and radical polymerization, ion polymerization, polycondensation, ring-opening polymerization, or the like can be suitably used. Furthermore, the solvent used in the polymerization may be appropriately selected depending on the monomer, and for example, water, phosphate buffer solution, Tris buffer solution, acetate buffer solution, methanol, ethanol, or the like can be suitably used.

The polymerization initiator is also not particularly limited, and for example, persulfates such as ammonium persulfate or sodium persulfate; hydrogen peroxide; peroxides such as t-butyl hydroperoxide or cumene hydroperoxide, azobisisobutyronitrile; benzoyl peroxide, or the like can be suitably used. Among these polymerization initiators, in particular, an initiator that exhibits an oxidative property, such as a persulfate or a peroxide, can also be used as a redox initiator with sodium bisulfite, N,N,N',N'-tetramethylethylenediamine, or the like. Alternatively, light, radioactive rays, or the like may be used as the initiator.

The polymerization temperature is not particularly limited, but is normally 5° C. to 80° C. The polymerization time is also not particularly limited, but is normally 4 hours to 48 hours.

Concentrations of the monomer, the cross-linking agent, and the like during polymerization are not particularly limited as long as they are concentrations at which the stimuli-responsive polymer, the hydrophilic polymer, or the cross-linked bodies thereof are obtained. In addition, the concentration of the polymerization initiator is also not particularly limited and may be selected as appropriate.

In the methods described in (1) and (2) above, the method in which the monomer is polymerized and cross-linked to form the cross-linked network of the cross-linked body of the stimuli-responsive polymer or the hydrophilic polymer may be a method of polymerizing the monomer in the presence of the cross-linking agent, or a method of polymerizing the monomer to form a polymer and then cross-linking the polymer with the cross-linking agent.

In the methods described in (1) and (2) above, in the first step, a polymerization condition or a cross-linking condition in which no cross-linking is formed between the polymer or the cross-linked body thereof formed in the second step only need be selected as appropriate.

The monomer constituting the stimuli-responsive polymer, the monomer constituting the hydrophilic polymer, and the cross-linking agent in the methods described in (1) and (2) above are as mentioned above in the description of the "cross-linked body of the temperature-responsive polymer" and the "cross-linked body of the hydrophilic polymer".

Furthermore, in the methods described in (1) and (2), the stimuli-responsive polymer or the cross-linked body thereof is produced (first step), and then the hydrophilic polymer or the cross-linked body thereof is produced in the presence of the obtained stimuli-responsive polymer or the cross-linked body thereof (second step). In the methods described in (1) and (2), this is not a limitation, and the hydrophilic polymer or the cross-linked body thereof may be produced, and then the stimuli-responsive polymer or the cross-linked body thereof may be produced in the presence of the obtained hydrophilic polymer or the cross-linked body thereof.

The polymer gel prepared as described above is dried to produce a dried body (drying step), and the dried body is caused to absorb a solution containing an active ingredient (absorption step).

In the preparation step, after a plurality of stimuli-responsive polymer materials or a single stimuli-responsive polymer material, which is a component of the impregnation material, and a plurality of hydrophilic polymers or a single hydrophilic polymer are mixed, each of them is cross-linked and gelled and, after this, the gel is immersed in an aqueous solution of the other and cross-linked in a state where the gel is impregnated with the aqueous solution, or only the other is cross-linked. In the drying step, the stimuli-responsive polymer gel having the IPN structure or the semi-IPN structure obtained by gelation is freeze-dried or heat-dried to form the dried body.

In the absorption step, the dried gel made of the stimuli-responsive polymer gel which has become the dried body is placed in a state with no external stimulus, and is impregnated with the solution containing the active ingredient by immersing the dried gel in the solution for impregnation or spraying the solution for impregnation on the dried gel. In the case of the temperature-responsive polymer gel, heat is applied as the external stimulus in use, and thus the polymer gel is impregnated with the solution containing the active ingredient by immersion or spraying in a temperature condition of the LCST or lower.

In the second production method, first, the stimuli-responsive polymer and the hydrophilic polymer, which are components of the stimuli-responsive polymer gel having the IPN structure, the semi-IPN structure, or the copolymer structure before cross-linking, and the active ingredient for impregnation are mixed to produce a mixture (mixing step), As described in a sixth embodiment to be described below, the active ingredient to be mixed here may be water-soluble, or may be water-insoluble or hydrophobic.

Next, a cross-linking component (cross-linking agent, cross-linking facilitator, or the like) is added to the mixture, or the mixture is immersed in the cross-linking agent to gel the mixture, thereby producing the stimuli-responsive polymer gel that is impregnated with the active ingredient (gelation step). At this time, what is made to have the gel structure by cross-linking is a component material of the impregnation material, and the active ingredient for impregnation is not cross-linked.

In the mixing step, the active ingredient is mixed in the process of mixing the plurality of stimuli-responsive polymer materials and the hydrophilic polymer material, which are components of the impregnation material. Then, the mixture is cross-linked and gelled in a state where the active ingredient is included in the polymer network structure.

In the gel produced by the second production method, the stimuli-responsive polymer gel including the active ingredient obtained by cross-linking may be used as is (while maintaining a wet state), or the stimuli-responsive polymer gel may be further dried (drying step). In the second production method, both when the gel is a dried body and when the gel is in a wet state, the gel includes the active ingredient, and if the gel is in a wet gel state, the active ingredient is released together with water by a stimulus. On the other hand, even if a dried body is used, when the gel is immersed in water, an appropriate amount of water is sprayed on the gel, or the gel is placed in a high humidity and low temperature (thereto-sensitive temperature or lower) environment, the gel absorbs water or moisture to be impregnated with a water-soluble active ingredient.

In the third production method, first, the hydrophilic polymer need not be used in the method of (3) of the preparation step described above. Furthermore, in this method, instead of cross-linking, the stimuli-responsive polymer may be mixed.

The polymer gel prepared in this manner is mixed with the active ingredient for impregnation to produce a mixture (mixing step).

Then, a cross-linking component (cross-linking agent, cross-linking facilitator, or the like) is added to the mixture, or the mixture is immersed in the cross-linking agent to gel the mixture, thereby producing the stimuli-responsive polymer gel that is impregnated with the active ingredient (gelation step). At this time, what is made to have the gel structure by cross-linking is a component material of the impregnation material, and the active ingredient for impregnation is not cross-linked.

In the fourth production method, first, the stimuli-responsive polymer and the active ingredient for impregnation are mixed to form a mixture (mixing step). Next, a cross-linking component (cross-linking agent, cross-linking facilitator, or the like) is added to the mixture, or the mixture is immersed in the cross-linking agent to gel the mixture, thereby producing the stimuli-responsive polymer gel that is impregnated with the active ingredient (gelation step). At this time as well, similarly to the gelation step in the third production method, what is made to have the gel structure by cross-linking is a component material of the impregnation material, and the active ingredient is not cross-linked.

Note that in the third and fourth production methods, the stimuli-responsive polymer may be dried after the gelation step (drying step).

In the fifth production method, first, the stimuli-responsive polymer is cross-linked or mixed to prepare the stimuli-responsive polymer gel (preparation step) in the same manner as in the third production method. Subsequently, the polymer gel thus prepared is dried to form a dried body (drying step). Then, the dried body is caused to absorb the solution containing the active ingredient (absorption step).

First Embodiment

A first embodiment of the present invention will be described below with reference to FIG. 1.

FIG. 1 is a perspective view illustrating a configuration of an impregnation material 1 according to the present embodiment.

As illustrated in FIG. 1, the impregnation material 1 is formed into a rectangular plate shape. The impregnation material 1 includes a temperature-responsive polymer gel 11 that is the temperature-responsive polymer gel described above. The temperature-responsive polymer gel 11 may constitute the impregnation material 1 by itself, or may be formed on a substrate (metal, plastic, wood, paper, or the like) to form the impregnation material 1.

The temperature-responsive polymer gel 11 is formed of a material or composition that has an LCST slightly lower than human body temperature (temperature of the skin).

In this way, the temperature-responsive polymer gel 11 having an LCST slightly lower than human body temperature exhibits hydrophilicity when the environmental temperature is less than the LCST and retains a solution containing an active ingredient such as a serum or a chemical solution. On the other hand, the temperature-responsive polymer gel 11 exhibits hydrophobicity when it is applied to human skin and warmed. When the temperature exceeds the LCST, the temperature-responsive polymer gel 11 releases the solution (active ingredient).

With this configuration, the impregnation material 1 can apply the active ingredient to the skin without being pressed or rubbed against the skin.

In addition, in cosmetic applications and medical applications, when the solution with which the impregnation material 1 is impregnated is lost, the impregnation material 1 is impregnated with the solution again under a temperature environment of less than the LCST. Therefore, the impregnation material 1 can be used a plurality of times in a single operation. Furthermore, when re-impregnated with the solution, the impregnation material 1 can be impregnated with different active ingredients, so that a different active ingredient can be applied each time.

Note that the impregnation material 1 is used by being held by a user, and thus when the temperature of a portion in contact with the hand is the LCST or higher, the impregnation material 1 releases the solution from that portion. To suppress such a disadvantage, the impregnation material 1 is preferably covered by a container or the like to expose only the portion that comes into contact with the skin and to not transmit the temperature of the hand to the periphery of the portion. Such a configuration may also be adopted for second to fifth embodiments described below.

Second Embodiment

A second embodiment of the present invention will be described below with reference to FIG. 2.

Figure 2:
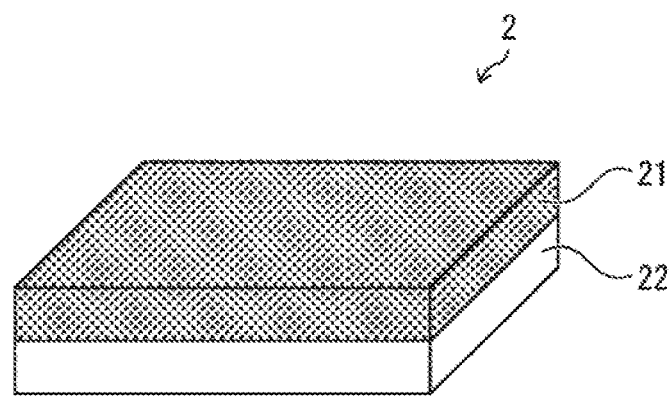
FIG. 2 is a perspective view illustrating a configuration of an impregnation material according to a second embodiment of the present invention.

FIG. 2 is a perspective view illustrating a configuration of an impregnation material 2 according to the present embodiment.

In a state where the environmental temperature is low, the impregnation material 1 according to the first embodiment described above can retain the solution while maintaining hydrophilicity unless the impregnation material 1 is warmed to a temperature higher than or equal to the LCST by touching the skin or the like. However, in a state where the environmental temperature is the LCST or higher, the impregnation material 1 has a disadvantage of releasing the solution even when the impregnation material 1 is not in contact with the skin.

In the present embodiment, a configuration that can suppress such a disadvantage will be described.

As illustrated in FIG. 2, the impregnation material 2 is formed into a rectangular plate shape. The impregnation material 2 includes a temperature-responsive polymer gel 21 that is the temperature-responsive polymer gel having the LCST described above, and a temperature-responsive polymer gel 22 (auxiliary stimuli-responsive polymer gel). The temperature-responsive polymer gels 21, 22 are layered.

As with the temperature-responsive polymer gel 21, the temperature-responsive polymer gel 22 is a stimuli-responsive polymer gel whose affinity with water reversibly changes in response to heat, and reversibly absorbs moisture and releases the absorbed moisture due to changes in temperature. However, the temperature-responsive polymer gel 22 differs from the temperature-responsive polymer gel 21 in that the temperature-responsive polymer gel 22 is a polymer gel having an upper critical solution temperature (UCST, in the description below, sometimes referred to as "UCST").

The temperature-responsive polymer gel 22 exhibits hydrophobicity at a low temperature that is less than the UCST of a predetermined level (phase change level), and exhibits hydrophilicity at a temperature of the UCST or higher. Here, in a case where, when a polymer is dissolved in water, the polymer is hydrophobic and dissolves at a low temperature and the polymer is hydrophilic and does not dissolve at a certain temperature or higher, the "UCST" refers to a temperature that serves as the boundary of the temperatures.

Furthermore, examples of the temperature-responsive polymer that constitutes the temperature-responsive polymer gel 22 include a betaine polymer, which is a zwitterionic polymer. The betaine polymer has both ionic groups of an amino group having a positive charge and a sulfonic acid group having a negative charge in the same side chain. Representative examples of the betaine polymer include polymers of sulfobetaine, carbobetaine, and phosphobetaine. Examples of the sulfobetaine polymer include a quaternary ester or amide of methacrylic acid, a quaternized polypyrrolidinium compound, ionene, polyvinylpyrrolidinium, and a polyvinylimidazolium compound.

When this sulfobetaine is cross-linked with methylenebisacrylamide or the like to be prepared, a gel exhibiting the UCST is obtained. An example of the gel is N,N-dimethyl acrylamide propyl ammonium propanesulfonate (DMAAPS). Furthermore, examples of the gel include a zwitterionic polymer, an amide or an ester of methacrylic acid, and a quaternized pyrrolidinium compound. For the zwitterionic polymer, the carbobetaine polymer also has a carboxyl group having a negative charge and an amino group having a positive charge in the same side chain, and includes a heterocyclic or aromatic vinyl compound from the structure. In the amide or ester of methacrylic acid, quaternized nitrogen is substituted by an alkoxy group having a different chain length. The quaternized pyrrolidinium compound includes a linear or branched alkyl carboxyl group.

One example of the carbobetaine polymer is ethyl-3-propylaminocrotonate acrylic acid (CROPRO-AA). One example of the phosphobetaine polymer is o-[[2-(methacryloyloxy)ethyloxy]phosphonyl]choline (2-methacryloyloxyethyl phosphoryl choline), so called MPC. The MPC includes a phosphoric acid group as an active anionic group, and a quaternized ammonium group as an active cationic group.

Other examples of the phosphobetaine polymer include an amphoteric polyelectrolyte and the like. The amphoteric polyelectrolyte is formed by copolymerization of sodium styrene sulfonate (SSS), which is a hydrophilic component with a negative charge, and vinyl benzyl trimethylammonium chloride (VBTA), which is a hydrophobic component with a positive charge. Furthermore, examples of the phosphobetaine polymer include a copolymer of a hydrogen bondable monomer and a hydrophobic monomer. Examples of such a copolymer include poly N-acryloylglycinamide, poly N-acryloylasparagineamide, polyacrylamide-co-acrylonitrile, and poly(N-vinyl imidazole-co-1-vinyl-2-hydroxymethyl imidazole).

Other examples of the temperature-responsive polymer include a polymer having uracil of a nucleobase in the side chain, a triblock copolymer of polyethylene oxide and poly-L-lactic acid, a gel that can be synthesized by copolymerizing a ureido group-containing monomer and a cross-linking agent monomer, a styrene-methacrylic acid copolymer, an orthochlorostyrene-parachlorostyrene copolymer, chlorinated polyethylene, and a derivative thereof. The ureido polymer can be obtained by adding potassium cyanate to a polymer having a primary amine, and poly (allylamine-co-allylurea) (PAU) can be prepared by ureidation of the primary amino group of polyallylamine with potassium cyanate. As with the IPN gel of PAAm and PAAc, with the IPN or semi-IPN, or copolymerization, of these UCST polymers and the hydrophilic polymer such as acrylic acid or alginic acid, it is possible to prepare the UCST gel that releases water at a low temperature under an appropriate condition and swells to absorb water at a high temperature. Various types of UCST gels exist other than the UCST gel mentioned herein and can be prepared by combining various materials.

Next, an example of the combination of setting the LCST of the temperature-responsive polymer gel 21 and setting the UCST of the temperature-responsive polymer gel 22 will be described. In this example, it is assumed that the body temperature is 37° C., the LCST is 33° C., and the UCST is 38° C.

When the environmental temperature is 27° C., the temperature-responsive polymer gel 21 exhibits hydrophilicity, while the temperature-responsive polymer gel 22 exhibits hydrophobicity. At this time, the temperature-responsive polymer gel 21 is in a swollen state in which the solution is retained, and the temperature-responsive polymer gel 22 is in a contracted state in which the solution is not absorbed.

In a state where the impregnation material 2 touches human skin, the temperature-responsive polymer gel 21 is warmed to a temperature above the LCST and exhibits hydrophobicity, thereby releasing the solution. On the other hand, the temperature-responsive polymer gel 22 is warmed only to a temperature less than the UCST and remains hydrophobic, and does not absorb the solution released from the temperature-responsive polymer gel 21. This causes the solution to exude from the impregnation material 2 to be applied to the skin.

When the impregnation material 2 is left to stand under an environmental temperature that exceeds body temperature (for example, 41° C.), the temperature-responsive polymer gel 21 is warmed to a temperature above the LCST to exhibit hydrophobicity, while the temperature-responsive polymer gel 22 is warmed to a temperature above the UCST to exhibit hydrophilicity. At this time, the temperature-responsive polymer gel 21 is in a contracted state in which the solution is not absorbed and releases the solution. On the other hand, the temperature-responsive polymer gel 22 is in a swollen state to absorb the solution released from the temperature-responsive polymer gel 21.

In this temperature environment, in a state where the impregnation material 2 touches human skin, the temperature of the temperature-responsive polymer gel 21 decreases to the temperature of the skin but remains above the LCST, so that the temperature-responsive polymer gel 21 remains in the contracted state. On the other hand, the temperature of the temperature-responsive polymer gel 22 decreases to less than the UCST, and thus the temperature-responsive polymer gel 22 changes from being hydrophilic to being hydrophobic to be in a contracted state, thereby releasing the retained solution. This causes the solution to exude from the impregnation material 2 to be applied to the skin. At this time, the temperature-responsive polymer gel 22 is mainly impregnated with the solution, and thus the temperature-responsive polymer gel 22 on the back surface with respect to the temperature-responsive polymer gel 21 om the front surface touches the skin. As a result, the solution is more effectively applied to the skin.

In addition, when the temperature of an environment where the impregnation material 2 is placed decreases from a high temperature as described above to a temperature below the LCST by transferring the impregnation material 2 to a cool place or the like, the temperature-responsive polymer gel 21 exhibits hydrophilicity, while the temperature-responsive polymer gel 22 exhibits hydrophobicity. At this time, the temperature-responsive polymer gel 22 enters a contracted state and releases the retained solution, while the temperature-responsive polymer gel 21 becomes hydrophilic and absorbs the solution released from the temperature-responsive polymer gel 22. When the impregnation material 2 that has been stored in a cool place touches the skin, the temperature-responsive polymer gel 21 transitions to being hydrophobic due to the temperature of the skin, thereby allowing the impregnated solution to exude and the solution to be applied to the skin.

As described above, the impregnation material 2 of the present embodiment includes the temperature-responsive polymer gel 21 having the LCST and the temperature-responsive polymer gel 22 having the UCST, the LCST and the UCST being different temperatures, and the temperature-responsive polymer gels 21, 22 being layered.

As a result, when the temperature as a stimulus is the LCST or higher, the solution released from the temperature-responsive polymer gel 21 can be absorbed by the temperature-responsive polymer gel 22. On the other hand, when the temperature is less than the UCST, the solution released from the temperature-responsive polymer gel 22 can be absorbed by the temperature-responsive polymer gel 21. This can reduce the disadvantage that it is impossible to recover the solution released by the temperature-responsive polymer gel 21 at an environmental temperature even when the impregnation material 2 does not touch the skin.

Third Embodiment

A third embodiment of the present invention will be described below with reference to FIGS. 3 to 7.

Figure 3:
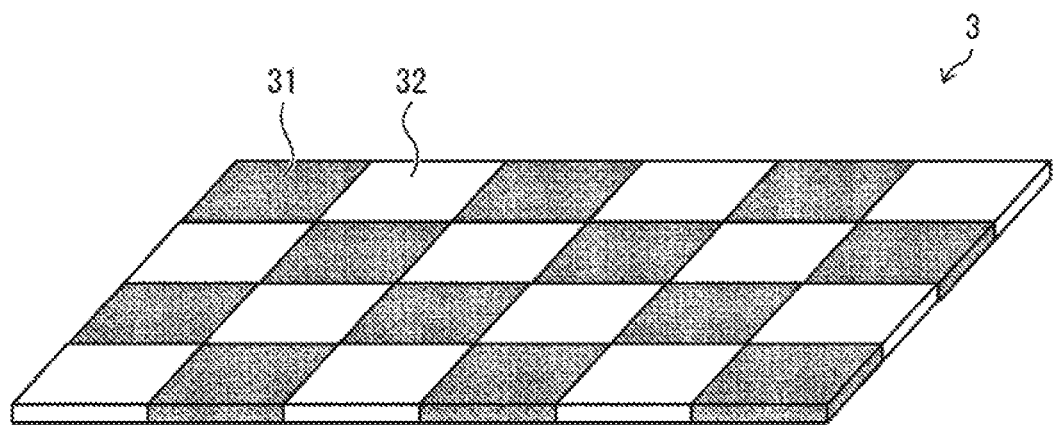
FIG. 3 is a perspective view illustrating a configuration of an impregnation material according to a third embodiment of the present invention.

FIG. 3 is a perspective view illustrating a configuration of an impregnation material 3 according to the present embodiment.

In the impregnation material 2 of the second embodiment described above, the direction in which the solution is released and absorbed between the temperature-responsive polymer gels 21, 22 is fixed, and transfer of the solution is only performed on the layered surfaces. For this reason, the transfer efficiency of the solution from the temperature-responsive polymer gel 21 to the temperature-responsive polymer gel 22 is not favorable, particularly when the environmental temperature becomes high. Thus, repeated changes in environmental temperature result in a disadvantage that the amount of the solution that can be supplied to the skin decreases.

In the present embodiment, a configuration that can prevent such a problem from occurring will be described.

As illustrated in FIG. 3, the impregnation material 3 is formed into a rectangular sheet shape. The impregnation material 3 includes a plurality of temperature-responsive polymer gels 31, each of which is the aforementioned temperature-responsive polymer gel, and a plurality of temperature-responsive polymer gels 32 (auxiliary stimuli-responsive polymer gel). The temperature-responsive polymer gels 31, 32 are disposed in a planar shape and are bonded to each other on side surfaces to form a flat plate. Furthermore, the temperature-responsive polymer gels 31, 32 are each formed in the same plate shape, and are arranged to alternate in the row direction and the column direction so as to form a checkerboard pattern.

The temperature-responsive polymer gels 31 are each a temperature-responsive polymer gel having the LCST, similar to the temperature-responsive polymer gel 21 in the second embodiment. The temperature-responsive polymer gels 32 are each a stimuli-responsive polymer gel having the UCST, similar to the temperature-responsive polymer gel 22 in the second embodiment.

Similarly to the impregnation material 2 of the second embodiment, in the impregnation material 3 configured as described above, the temperature-responsive polymer gels 32 can absorb the solution released from the temperature-responsive polymer gels 31 through the bonded surfaces of the temperature-responsive polymer gels 31, 32 when the temperature becomes the LCST or higher. In addition, in the impregnation material 3, when the temperature becomes less than the UCST, the temperature-responsive polymer gels 31 can absorb the solution released from the temperature-responsive polymer gels 32 through the bonded surfaces described above. This can reduce the disadvantage that it is impossible to recover the solution released by the temperature-responsive polymer gels 31 at an environmental temperature even when the impregnation material 3 does not touch the skin.

In addition, in the impregnation material 3, one of the temperature-responsive polymer gels 31 is in contact with the side surfaces of four temperature-responsive polymer gels 32 on the side surfaces, and one of the temperature-responsive polymer gels 32 is in contact with the side surfaces of four temperature-responsive polymer gels 31 on the side surfaces. In the temperature-responsive polymer gels 31, 32, the solution is free to move on the side surfaces.

For this reason, the temperature-responsive polymer gels 31, 32 are formed to be sufficiently smaller than the temperature-responsive polymer gels 21, 22 of the impregnation material 2. As a result, the contact area on the side surfaces of the temperature-responsive polymer gels 31, 32 can be greater than the contact area of the temperature-responsive polymer gels 21, 22. Thus, the solution can be efficiently transferred between the temperature-responsive polymer gels 31, 32.

It is also possible to adjust an amount of movement of moisture and moisture containing the active ingredient between the gels, for example, an amount of movement from the temperature-responsive polymer gels 31 to the temperature-responsive polymer gels 32, and an amount of movement from the temperature-responsive polymer gels 32 to the temperature-responsive polymer gels 31. In this case, in addition to a stimulus such as temperature, the shape of the gel interface also acts as a stimulus.

To increase the amount of movement of moisture, the bonded surfaces where the temperature-responsive polymer gels 31, 32 are bonded to each other are made wider than bonded surfaces perpendicular to the surfaces formed by bonding of the temperature-responsive polymer gels 31, 32. Examples of the method therefor include, rather than making the bonded surfaces perpendicular with respect to bottom surfaces of the temperature-responsive polymer gels 31, 32, inclining the bonded surfaces with respect to the bottom surfaces, and forming the bonded surfaces into a complex shape with irregularities.

The bonded surface is inclined by forming the temperature-responsive polymer gels 31, 32 so that each side surface is inclined, or by cutting the side surfaces of the temperature-responsive polymer gels 31, 32 obliquely. In addition, the bonded surface is formed into a concave-convex shape by forming a gel in a mold having irregularities, or the like. When the area of the bonded surface is increased in this way, the amount of movement of moisture between different gels is increased.

Conversely, in order to reduce the amount of movement of moisture, in addition to making the bonded surfaces perpendicular to the bottom surfaces, movement can be suppressed by interposing another gel even partly on the bonded surface, for example, a gel without stimuli responsiveness, or a gel that has stimuli responsiveness but contains no active ingredient. When a temperature-responsive polymer gel having a shielding property against movement of moisture to function as a so-called shutter is interposed between, for example, the temperature-responsive polymer gels 31, 32, the temperature-responsive polymer gel is referred to as a shielding polymer gel. When the temperature sensitive point of the shielding polymer gel is less than or equal to the temperature sensitive point of the temperature-responsive polymer gel 31, the change to being hydrophobic occurs earlier, and movement of moisture from the temperature-responsive polymer gel 31 to the temperature-responsive polymer gel 32 is prevented. The amount of movement can be controlled by the size of such a gel functioning as a shutter.

To make the shielding polymer gel, a polymer gel without stimuli responsiveness is inserted into the bonded surface of the temperature-responsive polymer gels 31, 32 and cross-linked, or a gel that undergoes a phase change by the same temperature stimulus is inserted into the bonded surface and cross-linked.

Note that in the present embodiment, the configuration has been described in which the plurality of temperature-responsive polymer gels 31 each having the LCST and the plurality of temperature-responsive polymer gels 32 each having the UCST are disposed in a mixed manner. This is not a limitation, and the impregnation material 3 may include only a plurality of the temperature-responsive polymer gels 31.

Furthermore, all the LCSTs of the plurality of temperature-responsive polymer gels 31 need not be the same, but some of the temperature-responsive polymer gels 31 may have a LCST different from that of the other of the temperature-responsive polymer gels 31. As a result, when the temperature (level of stimulus) is changed, the active ingredient can be released at different timings from the temperature-responsive polymer gels 31 having different LCSTs. This can extend the period of time during which the active ingredient is released. In addition, the temperature-responsive polymer gels 31 may be impregnated with solutions containing different active ingredients depending on the LCSTs. This allows different active ingredients to be released at different timings.

In the above case, as described above, when control is performed depending on shapes of bonded surfaces of the plurality of temperature-responsive polymer gels 31 having different LCSTs, mutual mixing of components of the respective temperature-responsive polymer gels 31 can be prevented. In addition, when the shielding polymer gel is used to intendedly mix an appropriate amount of the temperature-responsive polymer gels, components that have been separate components until just before can be mixed when applied to a target such as the skin.

Furthermore, in the present embodiment, it has been described that in order to increase the amount of movement of moisture, the bonded surface where the temperature-responsive polymer gels 31,32 are bonded to each other is made wider than the bonded surface perpendicular to the surface formed by the bonding of the temperature-responsive polymer gels 31, 32. In addition, the bonded surfaces of adjacent temperature-responsive polymer gels, each of which is equivalent to the temperature-responsive polymer gel 31, may be made wider than a bonded surface perpendicular to a surface formed by bonding of the temperature-responsive polymer gels. This can increase the amount of movement of moisture between these temperature-responsive polymer gels.

Next, modified examples of the present embodiment will be described.

Figure 4:
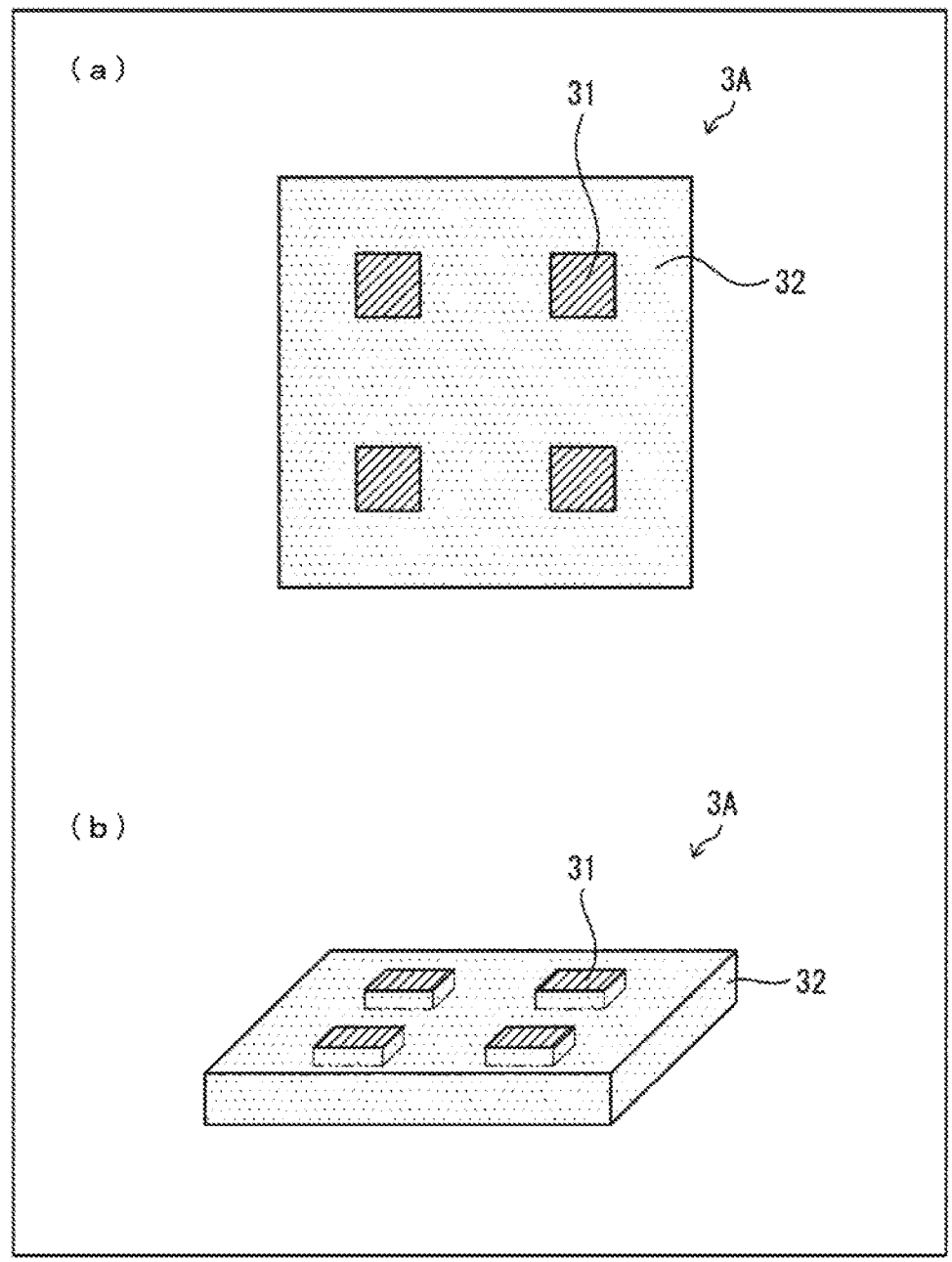
FIG. 4($a$) is a plan view illustrating a configuration of an impregnation material according to a first modified example of the third embodiment, and FIG. 4($b$) is a perspective view illustrating a configuration of the impregnation material.
Figure 5:
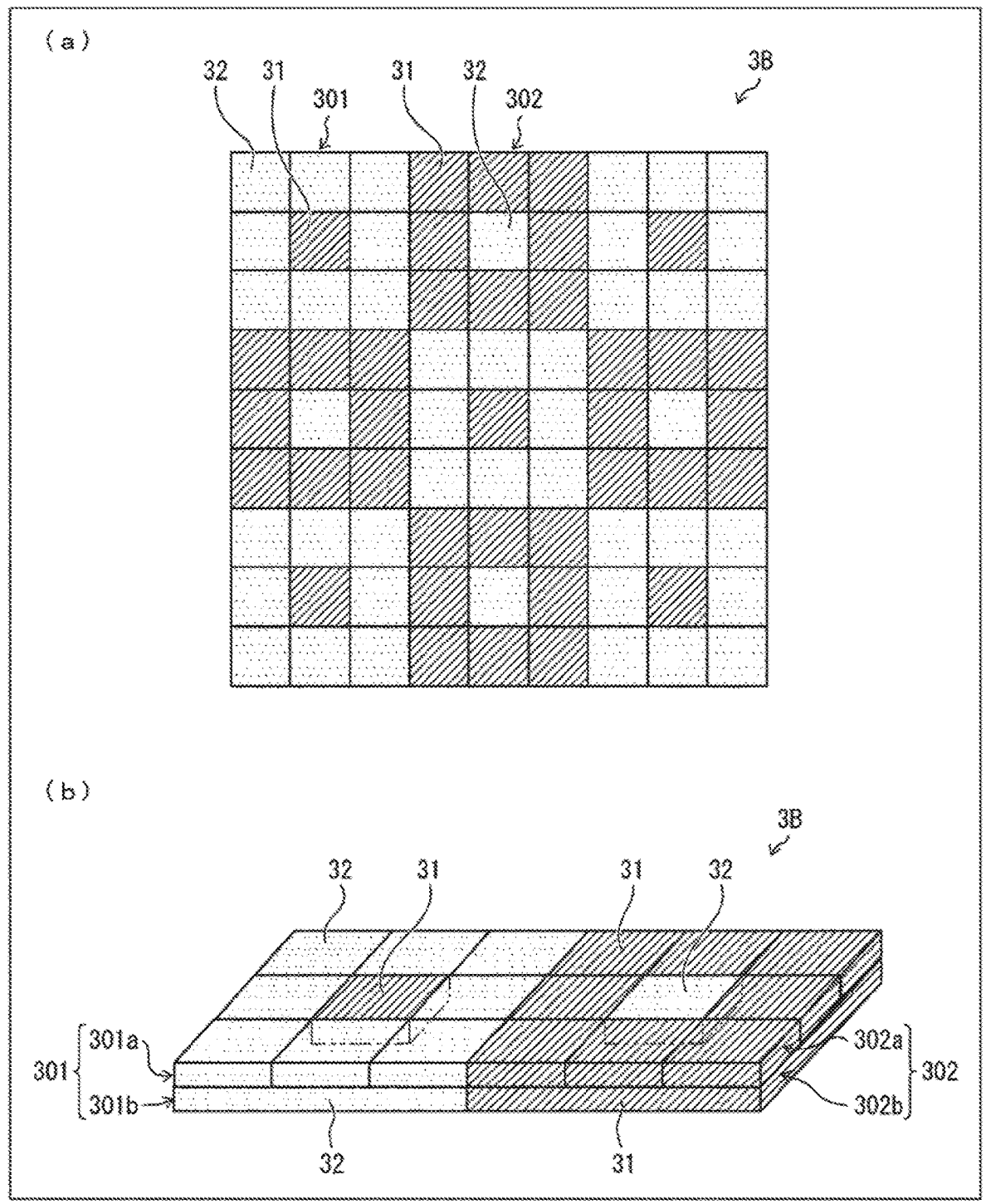
FIG. 5($a$) is a plan view illustrating a configuration of an impregnation material according to a second modified example of the third embodiment, and FIG. 5($b$) is a perspective view illustrating a configuration of the impregnation material.
Figure 6:
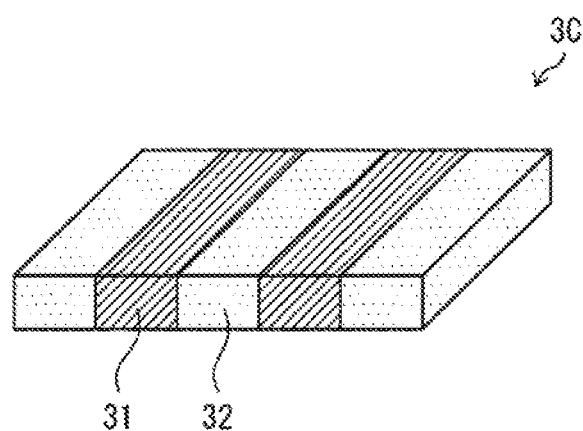
FIG. 6 is a perspective view illustrating a configuration of an impregnation material according to a third modified example of the third embodiment.
Figure 7:
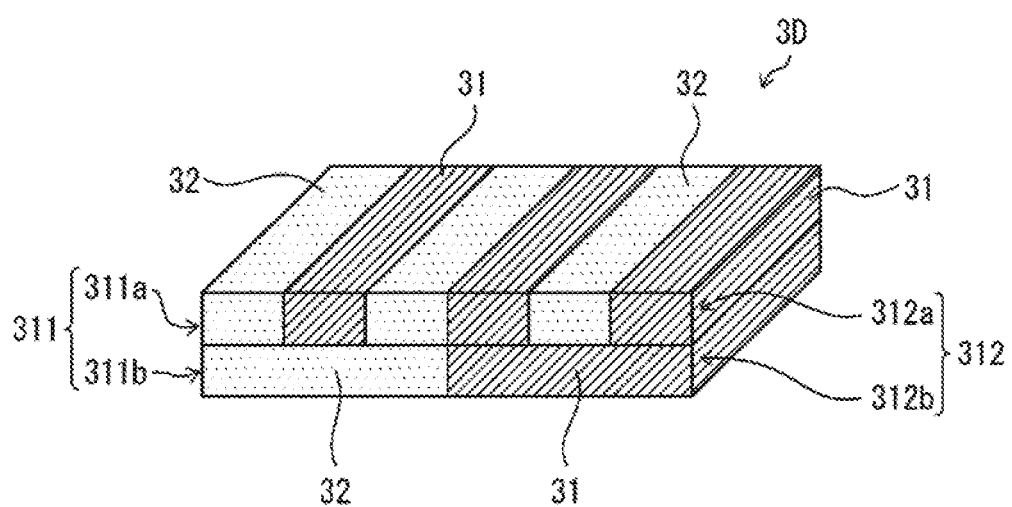
FIG. 7 is a perspective view illustrating a configuration of an impregnation material according to a fourth modified example of the third embodiment.

(a) of FIG. 4 is a plan view illustrating a configuration of an impregnation material 3A according to a first modified example, and (b) of FIG. 4 is a perspective view illustrating the configuration of the impregnation material 3A. (a) of FIG. 5 is a plan view illustrating a configuration of an impregnation material 3B according to a second modified example, and (b) of FIG. 5 is a perspective view illustrating the configuration of the impregnation material 3B. FIG. 6 is a perspective view illustrating a configuration of an impregnation material 3C according to a third modified example. FIG. 7 is a perspective view illustrating a configuration of an impregnation material 3D according to a fourth modified example.

The first modified example will be first described. As illustrated in (a) and (b) of FIG. 4, the impregnation material 3A according to the first modified example is formed into a rectangular sheet shape, and includes a plurality of temperature-responsive polymer gels 31 and a temperature-responsive polymer gel 32.

The temperature-responsive polymer gel 32 is formed into a rectangular shape forming the overall outline of the impregnation material 3A. The plurality of temperature-responsive polymer gels 31 are formed in a thickness ranging from the surface of the temperature-responsive polymer gel 32 to an intermediate position of the temperature-responsive polymer gel 32 in the thickness direction to be exposed on the surface of the temperature-responsive polymer gel 32. Furthermore, the temperature-responsive polymer gels 31 are aligned at a predetermined interval in an alternating manner, and are disposed at a predetermined interval with the outer peripheral end portion of the temperature-responsive polymer gel 32.

Note that in the example illustrated in (a) and (b) of FIG. 4, the impregnation material 3A has an islands-in-the-sea structure in which the temperature-responsive polymer gels 31 are dispersed in the temperature-responsive polymer gel 32. In contrast, although not illustrated, the impregnation material 3A may have an islands-in-the-sea structure in which the disposition relationship of the temperature-responsive polymer gels 31, 32 is reversed from that described above and the temperature-responsive polymer gels 32 are dispersed in the temperature-responsive polymer gel 31.

Next, the second modified example will be described. As illustrated in (a) and (b) of FIG. 5, the impregnation material 3B according to the second modified example is formed into a rectangular sheet shape. The impregnation material 3B includes a plurality of temperature-responsive polymer gels 31, each of which is the aforementioned temperature-responsive polymer gel, and a plurality of temperature-responsive polymer gels 32.

The impregnation material 3B includes a first section 301 and a second section 302, and has a structure in which the first section 301 and the second section 302 are bonded to each other on side surfaces. The first section 301 has an islands-in-the-sea structure that includes a larger number of the temperature-responsive polymer gels 32 with respect to the temperature-responsive polymer gel 31. The second section 302 has an islands-in-the-sea structure that includes a larger number of the temperature-responsive polymer gels 31 with respect to the temperature-responsive polymer gel 32.

The first section 301 includes a surface layer 301a and a base layer 301b provided on a lower side of the surface layer 301a. The second section 302 includes a surface layer 302a and a base layer 302b provided on a lower side of the surface layer 302a.

The surface layer 301a is formed of the temperature-responsive polymer gels 31, 32 each having a plate shape formed into an identical rectangular shape. In the surface layer 301a, the temperature-responsive polymer gels 31, 32 are disposed in a planar shape and bonded to each other on side surfaces to form a flat plate. Furthermore, the temperature-responsive polymer gels 31, 32 in the surface layer 301a are arranged, for example, in three columns and three rows, and one temperature-responsive polymer gel 31 is disposed in the center and eight temperature-responsive polymer gels 32 are disposed surrounding the periphery of the temperature-responsive polymer gel 31.

The base layer 301b is formed of the temperature-responsive polymer gel 32 and is formed into a flat plate having the same shape as the surface layer 301a.

The surface layer 302a is also formed of the temperature-responsive polymer gels 31, 32. In the surface layer 302a, the temperature-responsive polymer gels 31, 32 are disposed in a planar shape and bonded to each other on side surfaces to form a flat plate. Furthermore, the temperature-responsive polymer gels 31, 32 in the surface layer 302a are also arranged, for example, in three columns and three rows, and one temperature-responsive polymer gel 32 is disposed in the center and eight temperature-responsive polymer gels 31 are disposed surrounding the periphery of the temperature-responsive polymer gel 32.

The base layer 302b is formed of the temperature-responsive polymer gel 31 and is formed into a flat plate having the same shape as the surface layer 302a.

Next, the third modified example will be described. As illustrated in FIG. 6, the impregnation material 3C according to the third modified example is also formed into a rectangular sheet shape and includes a plurality of temperature-responsive polymer gels 31 and a plurality of temperature-responsive polymer gels 32. The temperature-responsive polymer gels 31, 32, each of which is formed into an elongated plate shape, are arranged in an alternating manner and bonded to each other on side surfaces on longer sides to form a striped structure, thereby forming a flat plate.

Furthermore, the fourth modified example will be described. As illustrated in FIG. 7, the impregnation material 3D according to the fourth modified example is also formed into a sheet shape and includes a plurality of temperature-responsive polymer gels 31 and a plurality of temperature-responsive polymer gels 32. The impregnation material 3D includes a first section 311 and a second section 312, and the first section 311 and the second section 312 are bonded to each other on side surfaces. The first section 311 has an islands-in-the-sea structure that includes a larger number of the temperature-responsive polymer gels 32 with respect to the temperature-responsive polymer gel 31. The second section 312 has an islands-in-the-sea structure that includes a larger number of the temperature-responsive polymer gels 31 with respect to the temperature-responsive polymer gel 32.

The first section 311 includes a surface layer 311a and a base layer 311b provided on a lower side of the surface layer 311a. The surface layer 311a is formed of the temperature-responsive polymer gels 31, 32 each formed into an elongated plate shape, and the temperature-responsive polymer gels 32 are disposed on both sides of the temperature-responsive polymer gel 31. The temperature-responsive polymer gels 31, 32 are bonded to each other on the side surfaces on the longer sides to form a flat plate. The base layer 311b is formed of the temperature-responsive polymer gel 32 and is formed into a flat plate having the same width and the same length as those of the surface layer 311a.

The second section 312 includes a surface layer 312a and a base layer 312b provided on a lower side of the surface layer 312a. The surface layer 312a is constituted by the temperature-responsive polymer gels 31, 32 each formed into an elongated plate shape, and the temperature-responsive polymer gels 31 are disposed on both sides of the temperature-responsive polymer gel 32. The temperature-responsive polymer gels 31, 32 are bonded to each other on the side surfaces on the longer sides to form a flat plate. The base layer 312b is formed of the temperature-responsive polymer gel 31 and is formed into a flat plate having the same width and the same length as those of the surface layer 312a.

Note that the base layer 311b need not have the same width and the same length as those of the surface layer 311a. Similarly, the base layer 312b need not have the same width and the same length as those of the surface layer 312a. From the perspective of water retention properties, it is more desirable that a size of the layer of the LCST be smaller than a size of the layer of the UCST. This is because, at the current technical level, an LCST material is more common and a good water-retentive material can be produced with the LCST material.

The impregnation materials 3A to 3D configured as described above can also achieve the aforementioned effects, similar to those of the impregnation material 3.

Fourth Embodiment

A fourth embodiment of the present invention will be described below with reference to FIG. 8.

Figure 8:
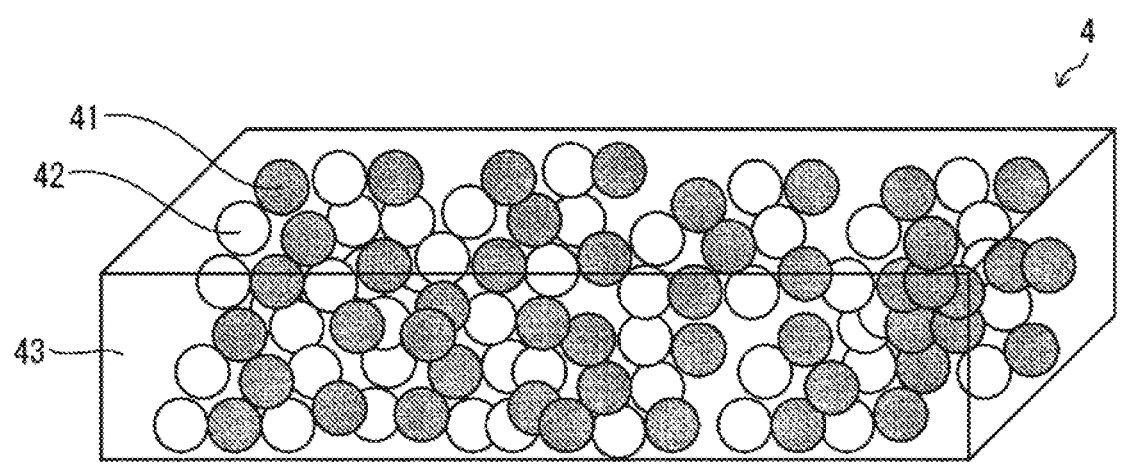
FIG. 8 is a perspective view illustrating a configuration of an impregnation material according to a fourth embodiment of the present invention.

FIG. 8 is a perspective view illustrating a configuration of an impregnation material 4 according to the present embodiment.

As illustrated in FIG. 8, the impregnation material 4 includes a plurality of temperature-responsive polymer gels 41, 42 and a water-permeable film 43 (permeable film). The temperature-responsive polymer gels 41, 42 are each formed into a particulate shape, and are dispersed so as to be randomly disposed within the water-permeable film 43, The temperature-responsive polymer gels 41, 42 can be formed into particulate shapes by a known method such as drop cross-linking of sol or emulsion polymerization.

The temperature-responsive polymer gels 41 are each a stimuli-responsive polymer gel having an LCST, similar to the temperature-responsive polymer gel 21 in the second embodiment. The temperature-responsive polymer gels 42 are each a stimuli-responsive polymer gel having a UCST, similar to the temperature-responsive polymer gel 22 in the second embodiment.

The water-permeable film 43 is a film through which moisture permeates, and a solution containing an active ingredient also permeates therethrough. The water-permeable film 43 is formed of a material such as a polymer film having water permeability. In addition, the water-permeable film 43 is preferably formed of a material having excellent biocompatibility from the perspective of being brought into contact with the skin.

The water-permeable film 43 may be composed of a porous material through which the active ingredient can permeate, such as a porous polymer sheet, mesh, gauze, or water-permeable fabric. The gel group (clusters of particulates) is wrapped with these materials, so that the temperature-responsive polymer gels 41, 42 each having a particulate shape can be randomly disposed. Alternatively, the impregnation material 4 may be configured by inserting or forming the temperature-responsive polymer gels 41, 42 in advance into a thicker, porous water-permeable film or a block.

In the impregnation material 4 thus configured, the temperature-responsive polymer gels 42 can absorb the solution released from the temperature-responsive polymer gels 41 when the temperature becomes the LCST or higher, similarly to the impregnation material 2 of the second embodiment. Meanwhile, in the impregnation material 4, the temperature-responsive polymer gels 41 can absorb the solution released from the temperature-responsive polymer gels 42 when the temperature becomes less than the UCST. This can reduce the disadvantage that it is impossible to recover the solution released by the temperature-responsive polymer gels 41 at an environmental temperature even when the impregnation material 4 does not touch the skin.

In addition, the temperature-responsive polymer gels 41, 42 each are formed into a particulate shape, and thus there is no directionality in the direction of absorption and release of the solution. As a result, the solution can be efficiently transferred between the temperature-responsive polymer gels 41, 42.

Note that in the impregnation material 4 of the present embodiment, a plurality of different temperature-responsive polymer gels 41, 42 are provided, but only a plurality of the temperature-responsive polymer gels 41 may be provided.

Furthermore, in a configuration in which only the plurality of temperature-responsive polymer gels 41 are provided, all LCSTs of the plurality of temperature-responsive polymer gels 41 need not be the same, but some of the temperature-responsive polymer gels 41 may have an LCST different from that of the other of the temperature-responsive polymer gels 41. As a result, when the environmental temperature is changed, the active ingredient can be released at different timings from the temperature-responsive polymer gels 41 having different LCSTs. This can extend the period of time during which the active ingredient is released. In addition, the temperature-responsive polymer gel 31 may be impregnated with a solution containing a different active ingredient depending on the LCST. This allows different active ingredients to be released at different timings.

Furthermore, when the temperature-responsive polymer gels 41, 42 are dispersed in sol rather than the water-permeable film 43, the impregnation material 4 can be used as an ointment.

Fifth Embodiment

A fifth embodiment of the present invention will be described below with reference to FIG. 9.

Figure 9:
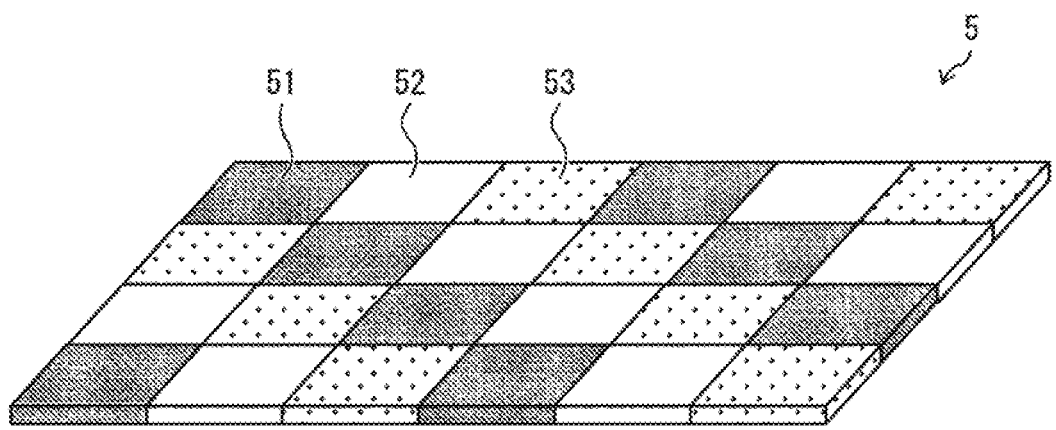
FIG. 9 is a perspective view illustrating a configuration of an impregnation material according to a fifth embodiment of the present invention.

FIG. 9 is a perspective view illustrating a configuration of an impregnation material 5 according to the present embodiment.

As illustrated in FIG. 9, the impregnation material 5 is formed into a rectangular sheet shape. The impregnation material 5 includes a plurality of temperature-responsive polymer gels 51 to 53 that are temperature-responsive polymer gels having an LCST, similar to the temperature-responsive polymer gel 21 in the second embodiment. The temperature-responsive polymer gels 51 to 53 are disposed in a planar shape and are bonded to each other on side surfaces to form a flat plate. Furthermore, the temperature-responsive polymer gels 51 to 53 are each formed into the same plate shape, and are arranged so as to appear in the same order in the row direction and the column direction and be bonded to different temperature-responsive polymer gels 51 to 53, respectively.

The temperature-responsive polymer gels 51 to 53 each have different LCSTs from each other. For example, the LCST of the temperature-responsive polymer gel 51 is 33° C., the LCST of the temperature-responsive polymer gel 52 is 38° C., and the LCST of the temperature-responsive polymer gel 53 is 41° C. These LCSTs are merely examples, and the LCSTs of the temperature-responsive polymer gels 51 to 53 are not limited to this example.

The impregnation material 5 thus configured includes the temperature-responsive polymer gels 51 to 53 having different LCSTs. As a result, when the environmental temperature is changed, an active ingredient can be released from the temperature-responsive polymer gels 51 to 53 having different LCSTs at different timings. This makes it possible to apply the active ingredient to the skin at different times. In addition, it is possible to provide an active ingredient corresponding to the temperature of an affected area or a site (heat generation caused by inflammation or the like) with surgical precision.

Specifically, when the surface of the impregnation material 5 touches the skin and the temperature of the impregnation material 5 becomes equal to or higher than the LCST of the temperature-responsive polymer gel 51 and less than the LCSTs of the temperature-responsive polymer gels 52, 53, the solution is released from the surface of the temperature-responsive polymer gel 51. In addition, when the impregnation material 5 is heated with a heater or the like and the temperature of the impregnation material 5 becomes equal to or higher than the LCST of the temperature-responsive polymer gel 52 and less than the LCST of the temperature-responsive polymer gel 53, the solution is released from the surface of the temperature-responsive polymer gel 52. Furthermore, when the heating temperature of the impregnation material 5 is increased and the temperature of the impregnation material 5 becomes equal to or higher than the LCST of the temperature-responsive polymer gel 53, the solution is released from the surface of the temperature-responsive polymer gel 53.

Here, it is assumed that the surface of the impregnation material 5 touches the skin and the temperature of the impregnation material 5 does not exceed the LCSTs of the temperature-responsive polymer gels 52, 53. In this state, the solution released from the temperature-responsive polymer gel 51 moves to the temperature-responsive polymer gels 52, 53 through the bonded surfaces between the temperature-responsive polymer gel 51 and the temperature-responsive polymer gels 52, 53. However, the temperature-responsive polymer gel 51 releases the solution from the surface directly touching the skin more than the side surfaces bonded to the temperature-responsive polymer gels 52, 53. As a result, the amount of movement of the solution from the temperature-responsive polymer gel 51 to the temperature-responsive polymer gels 52, 53 is small.

In addition, when the impregnation material 5 is left to stand at an environmental temperature of a high temperature equal to or higher than the LCST of the temperature-responsive polymer gel 53, release of the solution from the surfaces of the temperature-responsive polymer gels 51 to 53 and movement of the solution in the respective bonded surfaces occur over a wide range. Such a phenomenon does not occur in a temperature environment that is lower than human body temperature.

In the above temperature environment of a high temperature, a skin layer (hydrophobized layer) is formed on the surfaces of the hydrophobized temperature-responsive polymer gels 51 to 53. After the solution near the surface is released at an initial time in the temperature environment of a high temperature, the solution in inner portions of the temperature-responsive polymer gels 51 to 53 moves to an area having a high LC ST. That is, the solution of the temperature-responsive polymer gel 51 moves to the adjacent temperature-responsive polymer gel 52 and the solution of the temperature-responsive polymer gel 52 moves to the temperature-responsive polymer gel 53. Thus, not all the solution is released and loss of the solution that is released from the surface without being used can be suppressed.

The movement of moisture and moisture containing the active ingredient between the gels, for example, an amount of movement from the temperature-responsive polymer gel 51 to the temperature-responsive polymer gel 52 and an amount of movement from the temperature-responsive polymer gel 52 to the temperature-responsive polymer gel 53 can be adjusted in the same manner as in the third embodiment. In this case, in order to increase the amount of movement of moisture, the bonded surface where the temperature-responsive polymer gels 51, 52 are bonded to each other, or the bonded surface where the temperature-responsive polymer gels 52, 53 are bonded to each other is widened. In order to reduce the amount of movement of moisture, a shielding polymer gel is inserted to the respective bonded surfaces of the temperature-responsive polymer gels 51 to 53, in addition to making the bonded surface perpendicular to the bottom surface.

Note that the temperature-responsive polymer gels 51 to 53 may be impregnated with solutions containing different active ingredient, respectively. This allows the different active ingredients to be released from the temperature-responsive polymer gels 51 to 53 at different timings. In this case, as described above, when the release of the solution is controlled by the shapes of the bonded surfaces of the plurality of temperature-responsive polymer gels 51 to 53 having different LCSTs, it is possible to prevent components from being mixed with each other. In addition, when the shielding polymer gel is used to intendedly mix an appropriate amount of the temperature-responsive polymer gels, components that have been separate components until just before can be mixed when provided to a target such as the skin.

The impregnation material 5 includes the temperature-responsive polymer gels 51 to 53 having three types of LCSTs, but may also include two or four or more types of temperature-responsive polymer gels.

Alternatively, the stimuli-responsive polymer gel is made into a light-responsive polymer gel. As a result, control can be performed in such a manner that the active ingredient is released from only a portion irradiated with light that is controlled in a similar manner to or finer than that of the temperature-responsive polymer gel, or that release of the active ingredient is promoted or suppressed depending on the intensity of light. When the light-responsive polymer gel is used on a large surface or with surgical precision, it is possible to contribute to appropriate treatment of an affected area. Note that examples of the light-responsive polymer gel also include a temperature-responsive polymer gel having a material functioning as a photothermal converter added therein, such as carbon black, an electrically conductive polymer, or a metal particle.

Sixth Embodiment

A sixth embodiment of the present invention will be described below with reference to FIG. 10.

Figure 10:
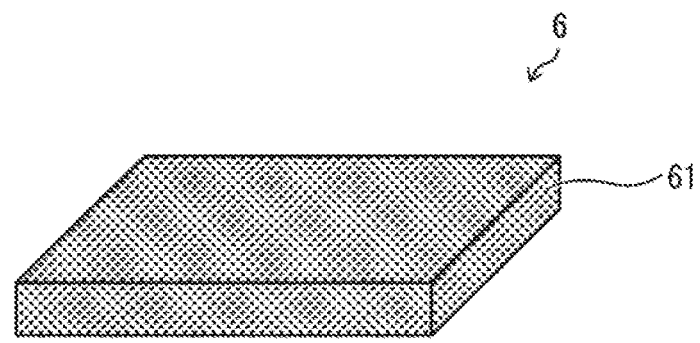
FIG. 10 is a perspective view illustrating a configuration of an application member according to a sixth embodiment of the present invention.

FIG. 10 is a perspective view illustrating a configuration of an application member 6 according to the present embodiment.

As illustrated in FIG. 10, the application member 6 is formed in a rectangular plate shape. The application member 6 is composed of an absorber 61 including a stimuli-responsive polymer that reversibly changes to being hydrophilic and to being hydrophobic in response to an external stimulus.

Examples of the stimuli-responsive polymer include a polymer constituting the stimuli-responsive polymer gel described above so as to allow impregnation and release of an active ingredient to be applied to the skin. When a degree of the external stimulus is less than a predetermined level, the stimuli-responsive polymer is highly likely to absorb moisture, and when the degree of the external stimulus is the predetermined level or greater, the stimuli-responsive polymer is highly likely to release moisture.

The active ingredient is a cosmetically effective cosmetic ingredient, a pharmaceutically effective medicinal component, or the like as described above, which is often water-soluble, but even though the active ingredient is water-insoluble, oil-based, or hydrophobic, when a surfactant is appropriately used, the gel can be impregnated with or include the active ingredient therein. For example, if a surfactant is used to use a double layer including a hydrophilic group and a hydrophobic group, when a gel is impregnated with an active ingredient, the active ingredient is introduced together with the surrounding water and water soluble components, and is released along with contraction of the gel when the gel is stimulated to undergo phase transition. Also in a case where an active ingredient is introduced during gel preparation, the active ingredient is introduced to a dried gel by swelling with moisture by moisture absorption or spraying, and is then released along with contraction of the gel stimulated. Furthermore, it is possible to cause the active ingredient, which is water-insoluble or oil-based, to be contained a water-soluble component using an emulsion.

The application member 6 configured as described above is likely to retain an active ingredient such as a serum or chemical solution in a state where a degree of an external stimulus is less than a predetermined level, while the application member 6 is likely to release the active ingredient in a state where the degree of the external stimulus is the predetermined level or greater. As a result, when the application member 6 is not used, the stimulus to be applied to the application member 6 is made less than the predetermined level, whereby the impregnation material easily retains the active ingredient. On the other hand, the stimulus of the predetermined level or greater is applied to the application member 6, whereby the impregnation material easily releases the active ingredient.

Furthermore, the external stimulus is heat, and thus, for example, when the human body temperature (temperature of the skin) is used as the external stimulus, it is possible to release the active ingredient with which the application member is impregnated only by bringing the application member into contact with the skin. In a state where an affected area has an elevated temperature, for example, when a person has a high fever, when a person has a cold, or when some inflammation continues, it is possible to release the active ingredient only to the affected area.

As described above, a user can use the application member 6 by being impregnated with a solution as described above including a desired active ingredient depending on the application. Thus, the application member 6 can be suitably used for beauty applications, medical applications, and the like for providing an active ingredient to the skin. It goes without saying that an active ingredient can be applied to the skin without being pressed or rubbed against the skin, similarly to the impregnation materials 1 to 5 described above.

Supplement

An application member according to a first aspect of the present invention includes a stimuli-responsive polymer that reversibly changes to being hydrophilic and to being hydrophobic in response to an external stimulus to allow impregnation and release of an active ingredient to be applied to the skin.

According to the above configuration, impregnation and release of the active ingredient are possible by applying an appropriate external stimulus.

An application member according to a second aspect of the present invention may be highly likely to absorb moisture when a degree of the external stimulus is less than a predetermined level, and may be highly to release moisture when the degree of the external stimulus is the predetermined level or greater in the first aspect.

According to the above configuration, an active ingredient of a serum, a chemical solution, or the like is easily retained in a state in which a degree of an external stimulus is less than a predetermined level, while the active ingredient is easily released in a state in which the degree of the external stimulus is the predetermined level or greater. As a result, when the application member is not used, an active ingredient is easily retained in the impregnation material by making a stimulus to be applied to the application member 6 less than a predetermined level. In addition, it is possible to facilitate release of the active ingredient from the impregnation material by applying a stimulus of a predetermined level or greater to the application member.

In an application member according to a third aspect of the present invention, the active ingredient may be water-soluble, water-insoluble, oil-based, or hydrophobic in the first or second aspect.

According to the above configuration, it is possible to easily impregnate the application member with the active ingredient.

In an application member according to a fourth aspect of the present invention, the external stimulus may be heat or light in any one of the first to third aspects.

According to the above configuration, it is also possible to release the active ingredient with which the application member is impregnated only by bringing the application member into contact with the skin when the human body temperature (temperature of the skin) is used as the external stimulus, for example. Furthermore, itis also possible to release the active ingredient with which the application member is impregnated by irradiating an affected area with light.

An impregnation material according to a fifth aspect of the present invention is impregnated with an active ingredient and includes a stimuli-responsive polymer gel (temperature-responsive polymer gels 11, 21, 31, 41, 51 to 53) absorbing the active ingredient in a state where a degree of an external stimulus is less than a predetermined level while releasing the active ingredient in a state where the degree of the external stimulus is the level or greater.

According to the above configuration, the impregnation material retains an active ingredient of a serum, a chemical solution, or the like in a state in which a degree of an external stimulus is less than a predetermined level, and releases the active ingredient in a state in which the degree of the external stimulus is the predetermined level or greater. As a result, when the impregnation material is not used, the active ingredient is retained in the impregnation material by making a stimulus to be applied to the impregnation material less than a predetermined level. In addition, it is possible to release the active ingredient from the impregnation material by applying a stimulus of a predetermined level or greater to the impregnation material.

In an impregnation material according to a sixth aspect of the present invention, the external stimulus may be heat or light in the fifth aspect.

According to the above configuration, the impregnation material retains an active ingredient of a serum, a chemical solution, or the like in a state in which a temperature is less than a temperature as the level described above, and releases the active ingredient in a state in which the temperature is equal to or higher than the temperature as the level described above. As a result, for example, when the level described above is set to about the human body temperature (temperature of the skin), the temperature of the impregnation material exceeds the above level only by bringing the impregnation material into contact with the skin, so that it is possible to release the active ingredient from the impregnation material. Furthermore, it is also possible to release the active ingredient with which the impregnation material is impregnated by irradiating an affected area with light.

In an impregnation material according to a seventh aspect of the present invention, a plurality of the stimuli-responsive polymer gels may be disposed in a planar shape and may be bonded to each other in a planar shape, and the levels of the stimuli-responsive polymer gels may be different, in the above fifth or sixth aspect.

According to the above configuration, levels of the stimulus for releasing an active ingredient are different among the stimuli-responsive polymer gels. As a result, when the level of the stimulus is changed, it is possible to make timings at which the active ingredient is released from the stimuli-responsive polymer gels different. This can extend the period of time during which the active ingredient is released.

In an impregnation material according to an eighth aspect of the present invention, the plurality of the stimuli-responsive polymer gels may be disposed in a planar shape and bonded to each other, and some of the stimuli-responsive polymer gels may have the level different from that of the other of the stimuli-responsive polymer gels, in the above fifth or sixth aspect.

According to the above configuration, levels of the stimulus for releasing an active ingredient are different among the stimuli-responsive polymer gels. As a result, when the level of the stimulus is changed, it is possible to make timings at which the active ingredient is released from the stimuli-responsive polymer gels different. This can extend the period of time during which the active ingredient is released.

In an impregnation material according to a ninth aspect of the present invention, a plurality of the stimuli-responsive polymer gels may be each formed in a particulate shape and retained in a material through which an active ingredient can permeate (a water-permeable film 43), and some of the stimuli-responsive polymer gels may have the level different from that of the other of the stimuli-responsive polymer gels, in the above fifth or sixth aspect.

According to the above configuration, some of the stimuli-responsive polymer gels have the level different from that of the other of the stimuli-responsive polymer gels, and thus when a degree of the stimulus is changed, it is possible to release the active ingredient from the stimuli-responsive polymer gels at different timings at which different levels are reached. This can extend the period of time during which the active ingredient is released.

In an impregnation material according to a tenth aspect of the present invention, the stimuli-responsive polymer gels may contain different active ingredients depending on the levels, in any one of the seventh to ninth aspects.

According to the above configuration, when the level of the stimulus is changed, it is possible to release different active ingredients from the respective stimuli-responsive polymer gels at different timings.

An impregnation material according to an eleventh aspect of the present invention may further include an auxiliary stimuli-responsive polymer gel (temperature-responsive polymer gels 22, 32, 42) that releases the active ingredient in a state in which an intensity of the external stimulus is less than a predetermined phase change level different from the level and meanwhile releases the active ingredient in a state in which the intensity of the external stimulus is the phase change level or greater, in the fifth or sixth aspect.

According to the above configuration, the level at which the stimuli-responsive polymer gel changes properties differs from the phase change level at which the auxiliary stimuli-responsive polymer gel changes properties. This allows the active ingredient released from the stimuli-responsive polymer gel to be absorbed in the auxiliary stimuli-responsive polymer gel when the stimulus is the level or greater. In addition, this also allows the active ingredient released from the auxiliary stimuli-responsive polymer gel to be absorbed in the stimuli-responsive polymer gel when the stimulus is less than the level.

In an impregnation material according to a twelfth aspect of the present invention, the stimuli-responsive polymer gel and the auxiliary stimuli-responsive polymer gel may be laminated, in the eleventh aspect.

According to the above configuration, transfer of the active ingredient is performed between the stimuli-responsive polymer gel and the auxiliary stimuli-responsive polymer gel.

In an impregnation material according to a thirteenth aspect of the present invention, a plurality of the stimuli-responsive polymer gels and a plurality of auxiliary stimuli-responsive polymer gels may be disposed to form a flat plate and may be in contact with each other, in the eleventh aspect.

According to the above configuration, transfer of the active ingredient is performed between the stimuli-responsive polymer gel and the auxiliary stimuli-responsive polymer gel. In addition, the stimuli-responsive polymer gels and the auxiliary stimuli-responsive polymer gels formed into a flat plate shape relatively easily move the active ingredient in a lateral direction, so that it is possible to efficiently transfer the active ingredient between the stimuli-responsive polymer gels and the auxiliary stimuli-responsive polymer gels.

In an impregnation material according to a fourteenth aspect of the present invention, a bonded surface where the stimuli-responsive polymer gel and the auxiliary stimuli-responsive polymer gel are bonded to each other may be wider than a bonded surface perpendicular to a surface formed by bonding the stimuli-responsive polymer gel and the auxiliary stimuli-responsive polymer gel, in the thirteenth aspect.

According to the above configuration, control can be performed to promote movement of the active ingredient between the stimuli-responsive polymer gel and the auxiliary stimuli-responsive polymer gel.

In an impregnation material according to a fifteenth aspect of the present invention, a shielding polymer gel having shielding properties for movement of moisture may be provided between the stimuli-responsive polymer gel and the auxiliary stimuli-responsive polymer gel, in the thirteenth aspect.

According to the above configuration, control can be performed to suppress movement of the active ingredient between the stimuli-responsive polymer gel and the auxiliary stimuli-responsive polymer gel.

In an impregnation material according to a sixteenth aspect of the present invention, the stimuli-responsive polymer gel and the auxiliary stimuli-responsive polymer gel may be each formed in a particulate shape and held in a permeable film through which the active ingredient can permeate, in the eleventh aspect.

According to the above configuration, the stimuli-responsive polymer gel and the auxiliary stimuli-responsive polymer gel each formed in a particulate shape have no directionality in a direction of absorption and release of the active ingredient. As a result, it is possible to efficiently transfer the active ingredient between the stimuli-responsive polymer gel and the auxiliary stimuli-responsive polymer gel.

A method for producing an impregnation material according to a seventeenth aspect of the present invention is a method for producing an impregnation material, which produces the impregnation material described in any one of the fifth to sixteenth aspects, the method including: a preparation step of cross-linking at least one of a stimuli-responsive polymer and a hydrophilic polymer to prepare the stimuli-responsive polymer gel; a drying step of drying the stimuli-responsive polymer gel to produce a dried body; and an absorption step of causing the dried body to absorb the active ingredient.

Alternatively, the production method may include a mixing step of mixing the stimuli-responsive polymer constituting the stimuli-responsive polymer gel and the active ingredient to produce a mixture, and a gelation step of gelling the mixture to producing the stimuli-responsive polymer gel that is impregnated with the active ingredient, in place of the drying step and the absorption step.

A method for producing an impregnation material according to an eighteenth aspect of the present invention is a method for producing an impregnation material, which produces the impregnation material described in any one of the fifth to sixteenth aspects, the method including: a mixing step of mixing a stimuli-responsive polymer, a hydrophilic polymer, and the active ingredient to produce a mixture; and a gelation step of cross-linking both the stimuli-responsive polymer and the hydrophilic polymer in the mixture together or cross-linking one of the stimuli-responsive polymer and the hydrophilic polymer in the mixture to gel the mixture to produce the stimuli-responsive polymer gel that is impregnated with the active ingredient, in a dried state or a semi-dried state.

A method for producing an impregnation material according to a nineteenth aspect of the present invention is a method for producing an impregnation material, which produces the impregnation material described in any one of the fifth to sixteenth aspects, the method including: a preparation step of cross-linking or mixing a stimuli-responsive polymer to prepare the stimuli-responsive polymer gel; a mixing step of mixing the stimuli-responsive polymer constituting the stimuli-responsive polymer gel and the active ingredient to produce a mixture; and a gelation step of gelling the mixture to produce the stimuli-responsive polymer gel that is impregnated with the active ingredient.

A method for producing an impregnation material according to a twentieth aspect of the present invention is a method for producing an impregnation material, which produces the impregnation material described in any one of the fifth to sixteenth aspects, the method including: a mixing step of mixing a stimuli-responsive polymer and the active ingredient to produce a mixture; and a gelation step of cross-linking the stimuli-responsive polymer in the mixture to gel the mixture to produce the stimuli-responsive polymer gel that is impregnated with the active ingredient.

A method for producing an impregnation material according to a twenty-first aspect of the present invention may further include a drying step of drying the stimuli-responsive polymer gel in the nineteenth or twentieth aspect.

A method for producing an impregnation material according to a twenty-second aspect of the present invention is a method for producing an impregnation material, which produces the impregnation material described in any one of the fifth to sixteenth aspects, the method including: a preparation step of cross-linking or mixing a stimuli-responsive polymer to prepare the stimuli-responsive polymer gel; a drying step of drying the stimuli-responsive polymer gel to produce a dried body; and an absorption step of causing the dried body to absorb the active ingredient.

Supplementary Information

The present invention is not limited to each of the above-described embodiments. It is possible to make various modifications within the scope of the claims. An embodiment obtained by appropriately combining technical elements each disclosed in different embodiments falls also within the technical scope of the present invention. Furthermore, technical elements disclosed in the respective embodiments may be combined to provide a new technical feature.

The invention claimed is:

1. An impregnation material impregnated with an active ingredient, the impregnation material comprising:
   a stimuli-responsive polymer gel that absorbs the active ingredient in a state in which a degree of an external stimulus is less than a predetermined level, and that releases the active ingredient in a state in which the degree of the external stimulus is greater than or equal to the predetermined level,
   wherein a plurality of stimuli-responsive polymer gels including the stimuli-responsive polymer gel are disposed in a planar shape and are bonded to each other, and
   the predetermined level of the external stimulus of some a first set of the plurality of stimuli-responsive polymer gels is different from the predetermined level of the external stimulus of a second set of the plurality of stimuli-responsive polymer gels.

2. An impregnation material impregnated with an active ingredient, the impregnation material comprising:
   a stimuli-responsive polymer gel that absorbs the active ingredient in a state in which a degree of an external stimulus is less than a predetermined level, and that releases the active ingredient in a state in which the degree of the external stimulus is greater than or equal to the predetermined level,
   wherein the stimuli-responsive polymer gel is formed into a particulate shape, and a plurality of stimuli-responsive polymer gels including the stimuli-responsive polymer gel are provided and held in a material through which the active ingredient is capable of permeating, and
   the predetermined level of the external stimulus of a first set of the plurality of stimuli-responsive polymer gels is different from the predetermined level of the external stimulus of a second set of the plurality of stimuli-responsive polymer gels.

3. An impregnation material, comprising:
   an active ingredient; and
   a stimuli-responsive polymer gel comprising (i) a stimuli-responsive polymer that exhibits hydrophilicity in a state in which a degree of an external stimulus is less than a predetermined level, and that exhibits the hydrophobicity in a state in which the degree of the external stimulus is greater than or equal to the predetermined level, and (ii) a hydrophilic polymer, wherein the stimuli-responsive polymer and the hydrophilic polymer form an interpenetrating polymer network structure or a semi-interpenetrating polymer network structure.

4. The impregnation material according to claim 3, further comprising:
a plurality of stimuli-responsive polymer gels including the stimuli-responsive polymer gel,
wherein the predetermined level of the external stimulus of a first set of the plurality of stimuli-responsive polymer gels is different from the predetermined level of the external stimulus of a second set of the plurality of stimuli-responsive polymer gels.

5. The impregnation material according to claim 4,
wherein the first set of the plurality of stimuli-responsive polymer gels is arranged to come into contact with the second set of the plurality of stimuli-responsive polymer gels.

6. The impregnation material according to claim 4,
wherein the first set of the plurality of stimuli-responsive polymer gels includes different types of an active ingredient from an active ingredient of the second set of the plurality of stimuli-responsive polymer gels.

* * * * *